United States Patent
Ma

(10) Patent No.: US 10,816,460 B2
(45) Date of Patent: Oct. 27, 2020

(54) METHOD AND DEVICE FOR MEASURING LIFESPAN OF RED BLOOD CELL

(71) Applicant: Shenzhen Seekya Bio-Sci & Tech Co., Ltd., Shenzhen, Guangdong (CN)

(72) Inventor: Yongjian Ma, Guangdong (CN)

(73) Assignee: Shenzhen Seekya Bio-Sci & Tech Co., Ltd., Shenzhen (CN)

( * ) Notice: Subject to any disclaimer, the term of this patent is extended or adjusted under 35 U.S.C. 154(b) by 258 days.

(21) Appl. No.: 16/079,615

(22) PCT Filed: Aug. 15, 2016

(86) PCT No.: PCT/CN2016/095337
§ 371 (c)(1),
(2) Date: Aug. 24, 2018

(87) PCT Pub. No.: WO2017/143739
PCT Pub. Date: Aug. 31, 2017

(65) Prior Publication Data
US 2019/0056318 A1    Feb. 21, 2019

(30) Foreign Application Priority Data

Feb. 26, 2016 (CN) .......................... 2016 1 0109023

(51) Int. Cl.
*G01N 21/3504* (2014.01)
*A61B 5/08* (2006.01)
(Continued)

(52) U.S. Cl.
CPC ......... *G01N 21/3504* (2013.01); *A61B 5/082* (2013.01); *A61B 5/145* (2013.01);
(Continued)

(58) Field of Classification Search
None
See application file for complete search history.

(56) References Cited

U.S. PATENT DOCUMENTS 6,248,078 B1 * 6/2001 Risby ............... A61B 5/097
600/529
7,445,601 B2 * 11/2008 Kline ............... A61B 5/417
600/529

(Continued)

OTHER PUBLICATIONS

Furne, Julie et al, "Simplification of the end-alveolar carbon monoxide technique to assess erythrocyte survival", Journal of Laboratory and Clinical Medicine, vol. 142, No. 1, Jul. 19, 2003, pp. 52-57. (Year: 2003).*

*Primary Examiner* — Matthew D Krcha

(57) ABSTRACT

A method and device for measuring the lifespan of a red blood cell is discussed. The method is a non-dispersive infrared spectrometry and comprises: injecting a small amount of sample at a constant speed; using an interference component absorption pack to remove interference components; measuring an alveolar gas sample and a background gas sample in pair and using a level difference-concentration difference fitting method to obtain the endogenous CO concentration in alveolar gas; using a dual-gas chamber method to measure the $CO_2$ concentration and the CO concentration; and removing the influence of air, which is mixed into the alveolar gas when the alveolar gas is acquired, on the measured value of the endogenous CO concentration in the alveolar gas according to the obtained $CO_2$ concentration, thereby obtaining the accurate value of the endogenous CO concentration in the alveolar gas and calculating the lifespan of the red blood cell.

20 Claims, 2 Drawing Sheets

(51) Int. Cl.
  *A61B 5/145* (2006.01)
  *A61K 35/18* (2015.01)
  *G01N 21/25* (2006.01)
  *G01N 21/27* (2006.01)

(52) U.S. Cl.
  CPC ........... *A61K 35/18* (2013.01); *G01N 21/255* (2013.01); *G01N 21/272* (2013.01); *G01N 21/274* (2013.01); *A61B 2560/0247* (2013.01)

(56) References Cited

U.S. PATENT DOCUMENTS

| | | | | |
|---|---|---|---|---|
| 8,074,646 B2* | 12/2011 | Daly | ................. | A61M 16/0045 128/204.18 |
| 9,789,133 B2* | 10/2017 | Wager | .................... | A61P 37/06 |
| 2004/0210154 A1* | 10/2004 | Kline | ................... | A61B 5/417 600/532 |
| 2009/0163825 A1* | 6/2009 | Hirsh | .................... | A61B 5/082 600/532 |
| 2010/0081955 A1* | 4/2010 | Wood, Jr. | ............... | A61B 5/097 600/532 |
| 2011/0208018 A1* | 8/2011 | Kiani | .................. | A61M 5/1723 600/301 |
| 2012/0288951 A1* | 11/2012 | Acharya | ............. | G01N 27/227 436/113 |
| 2014/0238399 A1* | 8/2014 | Daly | ................... | A61M 16/202 128/204.23 |
| 2015/0122260 A1* | 5/2015 | Daly | ................. | A61M 16/0875 128/204.23 |
| 2016/0033476 A1* | 2/2016 | Blake | ................. | G01N 33/497 73/23.3 |
| 2016/0153964 A1* | 6/2016 | Donnay | ............... | A61B 5/0836 600/326 |
| 2016/0256485 A1* | 9/2016 | Wager | .................... | A61P 11/06 |
| 2017/0074857 A1* | 3/2017 | Dennis | ................ | A61B 5/4833 |
| 2017/0191984 A1* | 7/2017 | Ma | ......................... | A61B 5/097 |

* cited by examiner

METHOD AND DEVICE FOR MEASURING LIFESPAN OF RED BLOOD CELL

TECHNICAL FIELD

The present disclosure relates generally to the technical field of medical diagnosis and more particularly, to a method and device for measuring the lifespan of the red blood cell.

BACKGROUND

The mammalian hematopoietic system has a special and important function of generating red blood cells which transport oxygen to various tissues of the animal body. The determination of the lifespan of the red blood cells can be used to identify the etiology of anemia and other diseases, to understand the pathogenesis of the disease and to judge the prognosis of the disease. Therefore, the lifespan measurement of the red blood cells is very important. The study has confirmed that the lifespan of the red blood cell can be calculated by accurately measuring the difference between the CO concentration of the exhaled pulmonary alveolus gas and the CO content in the air (environment gas) at the place where the subjects were located before the exhalation experiment. The common used methods for measuring the CO concentration in the air are non dispersive infrared spectroscopy, gas chromatography, electrochemical methods, mercury replacement method and so on. However, the existing methods have different defects, as some of which need too massive samples to be suitable for the exhalation measurement, some of which need too complicated operations to be suitable for the clinical use, and the others have poor repeatability and precision. Moreover, all those methods can only measure the CO concentration in the sample gas which is not the exhaled pulmonary alveolus gas. Moreover, the CO concentration in the exhaled pulmonary alveolus gas is not the endogenous CO concentration. The deviation of exhalation sample from the exhaled pulmonary alveolus gas is caused by the inevitable inflow of ambient gas during the gas extraction and/or intake, while the deviation of the CO concentration from the endogenous CO concentration in the exhaled pulmonary alveolus gas is caused by the CO in the environment.

There is no existing method or equipment that can measure the endogenous CO directly by a simple and convenient measurement and operation of the exhalation sample with a sufficient sensitivity and accuracy to determine the lifespan of the red blood cell. Accordingly, it is urgent to develop a special clinical diagnostic instrument for determining the lifespan of the red blood cell.

SUMMARY

The object of the present application is to provide a method and device for measuring the lifespan of the red blood cell, aiming at the above defects of the prior art that the existing method or equipment can measure the endogenous CO directly.

In one aspect, a method for measuring a lifespan of a red blood cell is provided, which employs at least one gas channel system each comprising a gas channel; a pulmonary alveolus gas bag, a background gas bag, a first reversing gas bag and a second reversing gas bag respectively connected to the gas channel via a respective solenoid valve; wherein each gas channel is connected to a same CO gas chamber, $CO_2$ gas chamber, cylinder piston assembly and air pump, wherein both of the CO gas chamber and the $CO_2$ gas chamber have an exhaust port and an inlet port with a solenoid valve, wherein the method for measuring the lifespan of a red blood cell comprises following steps.

For each gas channel system, steps S1-S6 are implemented sequentially:

S1) controlling the air pump to pump external air into the gas channel through a drying tube and a catalytic tube and finally into the $CO_2$ gas chamber, and then expelling the air in the $CO_2$ gas chamber through the exhaust port of the $CO_2$ gas chamber in a first time duration;

S2) controlling the cylinder piston assembly to deliver pulmonary alveolus gas from the pulmonary alveolus gas bag into the $CO_2$ gas chamber through the gas channel for determining its $CO_2$ concentration;

S3) controlling the cylinder piston assembly to deliver the pulmonary alveolus gas from the pulmonary alveolus gas bag into the first reversing gas bag through the gas channel;

S4) controlling the air pump to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration;

S5) controlling the cylinder piston assembly to deliver background gas from the background gas bag into the second reversing gas bag through the gas channel;

S6) controlling the air pump to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration.

After the implementation of the steps S1-S6, steps S7-S11 are implemented sequentially on each gas channel system:

S7) controlling the air pump to pump the external air into the gas channel through the drying tube and the catalytic tube and finally into the CO gas chamber, and then expelling the air in the CO gas chamber through the exhaust port of the CO gas chamber in a second time duration;

S8) delivering the background gas in the second reversing gas bag to the CO gas chamber with a small amount each time at an uniform velocity, or for multiple times of intermittence with a small amount each time at an uniform velocity for determining its CO concentration; wherein each time of gas delivery has a third time duration, and each intermittence of the multiple injections has a fourth time duration (It is noticed for that whether a multiple-injection is employed depends on the relationship between one injection volume of the cylinder and the volume of the reversing gas bag, and the relationship between one injection volume of the cylinder and the volume of the CO gas chamber. When the one injection volume is much less than the volume of the CO gas chamber, a multiple-injection with multiple times of intermittence and a small amount each time at an uniform velocity can be employed);

S9) controlling the air pump to pump the external air into the gas channel through the drying tube and the catalytic tube and finally into the CO gas chamber, and then expelling the air in the CO gas chamber through the exhaust port of the CO gas chamber in a second time duration;

S10) controlling the cylinder piston assembly to deliver the pulmonary alveolus gas in the first reversing gas bag to the CO gas chamber with a small amount each time at an uniform velocity, or for multiple times of intermittence with a small amount each time at an uniform velocity for determining its CO concentration; wherein each time of gas delivery has the third time duration, and each intermittence has the fourth time duration;

S11) controlling the air pump to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration.

After the implementation of the steps S7-S11, step S12 is implemented on a first gas channel system:

S12) controlling the air pump to pump the external air into the gas channel of the first gas channel system through the drying tube and the catalytic tube and finally into the CO gas chamber, and then expelling the air in the CO gas chamber through the exhaust port of the CO gas chamber in a second time duration.

In the method for measuring the lifespan of a red blood cell, the first time duration is 6-600s, the second time duration is 20-2000s, the third time duration is 1-90s and the fourth time duration is 1-100s.

In the method for measuring the lifespan of a red blood cell, for the i-th (i=1, 2, 3) gas channel system, its corresponding pulmonary alveolus gas bag, background gas bag, first reversing gas bag, and second reversing gas bag are respectively connected to the gas channel system via the solenoid valves Ei2, Ei3, Ei4, Ei5. In the method for measuring the lifespan of a red blood cell, the CO gas chamber and the $CO_2$ gas chamber shared by each gas channel system are respectively connected to one terminal of each gas channel system via the solenoid valves E01, E02, while other terminal of the each gas channel system is connected with one terminal of the air pump whose other terminal is connected to an gas inlet of cleaning gas through the drying tube and catalytic tube.

In another aspect, a device for measuring the lifespan of a red blood cell is provided, which consists of a gas chamber unit, a transmission unit, a circuit unit, a power source unit, a cleaning gas preparation unit, as well as a gas channel system and electrical connections connecting each unit. The gas chamber unit comprises one CO gas chamber assembly and one $CO_2$ gas chamber assembly, the transmission unit comprises a cylinder piston assembly pushed by a lead screw, a stepper motor assembly which drives the lead screw to rotate, the cleaning gas preparation unit comprises a gas pump assembly, a drying tube assembly and a catalytic tube assembly, and the circuit unit comprises a signal amplification, data processing, and control circuit including a programmable chip. The power source unit provides an electric source for satisfying each unit. The gas channel refers to connection gas pipes in the assemblies in each unit (including the solenoid valve controlling the on-off state of the gas channel) or between the unit assemblies and the gas bags (the pulmonary alveolus gas bag, the background gas bag, the first reversing gas bag and the second reversing gas bag). The gas channel system is composed of a common gas channel and a specific gas channel. Both of the CO gas chamber and the $CO_2$ gas chamber have an exhaust port and an inlet port with a solenoid valve. The pulmonary alveolus gas bag is used for loading pulmonary alveolus gas sampled from the subjects. The background gas bag is used for loading environment gas sampled at the place where the subjects are located. The first and second reversing gas bags are used as an absorption bag for removing ingredients in the pulmonary alveolus gas and the environment gas which interfere CO measurement. One group of gas bags including the pulmonary alveolus gas bag, the background gas bag, the first reversing gas bag and the second reversing gas bag, which are connected with gas chambers and transmission unit via the gas channels are together called as one measurement channel, which is short for one channel. Accordingly, the device for measuring the lifespan of a red blood cell can be a single-channel or multiple-channel which can be used to measure multiple groups of samples at the same time, while the other sample can be measured when the absorption bag is removing the interference ingredients, such that the waiting time is efficiently utilized and the time required for the whole measurement for each group of samples is greatly shorten. The device for measuring the lifespan of a red blood cell further comprises a control unit for each gas channel system to implement following steps S1-S6 sequentially:

S1) cleaning the gas channel and $CO_2$ gas chamber;

S2) controlling the cylinder piston assembly to deliver the pulmonary alveolus gas from the pulmonary alveolus gas bag into the $CO_2$ gas chamber through the gas channel for determining its $CO_2$ concentration;

S3) controlling the cylinder piston assembly to deliver the pulmonary alveolus gas from the pulmonary alveolus gas bag into the first reversing gas bag through the gas channel;

S4) cleaning the gas channel and $CO_2$ gas chamber;

S5) controlling the cylinder piston assembly to deliver background gas from the background gas bag into the second reversing gas bag through the gas channel;

S6) cleaning the gas channel and $CO_2$ gas chamber.

After the implementation of the steps S1-S6, steps S7-S11 are implemented sequentially on each gas channel system:

S7) cleaning the gas channel and CO gas chamber;

S8) delivering the background gas in the second reversing gas bag to the CO gas chamber with a small amount each time at an uniform velocity, or for multiple times of intermittence with a small amount each time at an uniform velocity for determining its CO concentration;

S9) cleaning the gas channel and CO gas chamber;

S10) controlling the cylinder piston assembly to deliver the pulmonary alveolus gas in the first reversing gas bag to the CO gas chamber with a small amount each time at an uniform velocity, or for multiple times of intermittence with a small amount each time at an uniform velocity for determining its CO concentration;

S11) cleaning the gas channel and $CO_2$ gas chamber.

After the implementation of the steps S7-S11, step S12 is implemented on a first gas channel system:

S12) cleaning the gas channel and CO gas chamber;

wherein the step of cleaning the gas channel and $CO_2$ gas chamber further comprises controlling the air pump to pump external air into the gas channel through the drying tube and the catalytic tube and finally into the $CO_2$ gas chamber, and then expelling the air in the $CO_2$ gas chamber through the exhaust port of the $CO_2$ gas chamber in a first time duration; and the step of cleaning the gas channel and CO gas chamber further comprises controlling the air pump to pump external air into the gas channel through the drying tube and the catalytic tube and finally into the CO gas chamber, and then expelling the air in the CO gas chamber through the exhaust port of the CO gas chamber in a second time duration.

In the device for measuring the lifespan of a red blood cell, the cylinder piston assembly comprises a lead screw, a cylinder communicating with the CO gas chamber, a piston-piston rod displaced inside the cylinder, a sliding block driving the piston rod to move along the screw rod in a reciprocating motion, and an electrical motor whose output shaft drives the sliding block to move the screw rod along a displacement of the lead screw.

In the device for measuring the lifespan of a red blood cell, for each gas channel system, the corresponding pulmonary alveolus gas bag, background gas bag, first reversing gas bag, and second reversing gas bag are respectively connected to the gas channel system via the solenoid valves Ei2, Ei3, Ei4, Ei5. The CO gas chamber and the $CO_2$ gas chamber shared by each gas channel system are respectively connected to one terminal of each gas channel system via the solenoid valves E01, E02, while other terminal of the each gas channel system is connected with one terminal of the air pump whose other terminal is connected to an gas inlet of cleaning gas through the drying tube and catalytic tube.

In the device for measuring the lifespan of a red blood cell, for each gas channel system, each gas channel system is connected with a gas outlet of the air pump through a solenoid valves Ei6.

In the device for measuring the lifespan of a red blood cell, each gas channel system is communicated with the CO gas chamber and the $CO_2$ gas chamber shared by them via the solenoid valves Ei1.

By the implementation of the present application, following effects can be obtained. The error effects of water vapor and CO in the environmental gas are eliminated through the drying tube and the catalytic tube, and a sampling process with a small amount each time at an uniform velocity, or for multiple times of intermittence with a small amount each time at an uniform velocity can be obtained through the cylinder, thus the measurement precision is high and the required sample quantity is few. In addition, the multiple-channel can measure multiple groups of samples at the same time which can shorten the measurement time of each group.

BRIEF DESCRIPTION OF THE DRAWINGS

In order to more clearly illustrate the embodiments of the present application, the present application is further illustrated combining the embodiments and drawings attached.

DETAILED DESCRIPTION OF THE PREFERRED EMBODIMENT

In order to clarify the objects, technical solutions and advantages of the embodiments of the present application, the following detailed description will be made for the technical solution in the embodiments of the present application.

Figure 1:
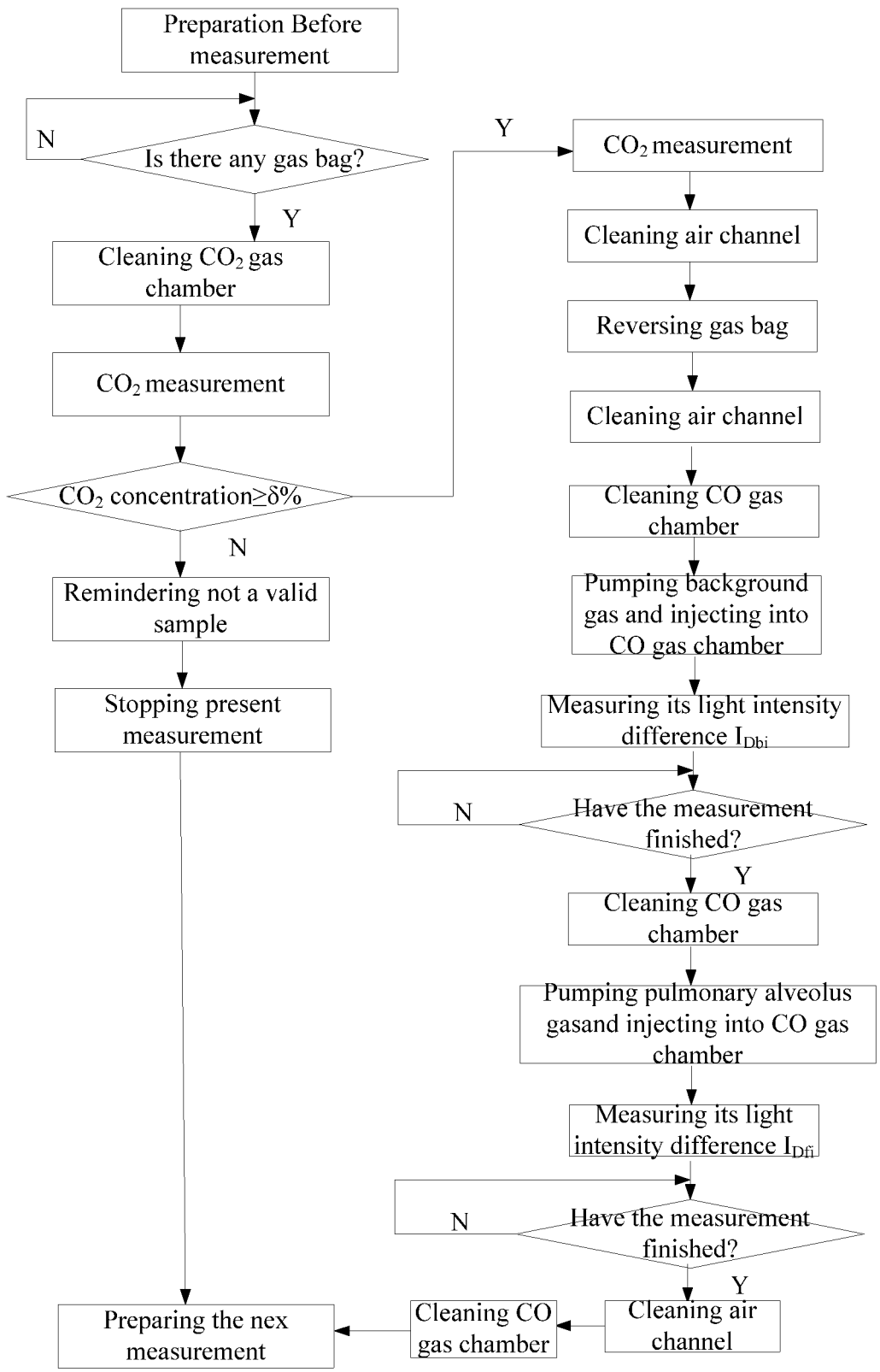
FIG. 1 is a flow diagram of the working principle of the method for measuring the lifespan of a red blood cell of the present application.

FIG. 1 has shown the working principle of the method for measuring the lifespan of a red blood cell of the present application. As shown in FIG. 1, before implementing the method for measuring the lifespan of a red blood cell of the present application, the existence of the pulmonary alveolus gas bag, the background gas bag, the first reversing gas bag and the second reversing gas bag is detected. The method for measuring the lifespan of a red blood cell of the present application has employed at least one gas channel system each comprising a gas channel; a pulmonary alveolus gas bag, a background gas bag, a first reversing gas bag and a second reversing gas bag respectively connected to the gas channel via a respective solenoid valve. Each gas channel is connected to a same CO gas chamber, $CO_2$ gas chamber, cylinder piston assembly and air pump. Both of the CO gas chamber and the $CO_2$ gas chamber have an exhaust port and an inlet port with a solenoid valve, wherein the method for measuring the lifespan of a red blood cell comprises following steps.

(1) Gas Channel Cleaning

The air pump is controlled to pump external air into the gas channel through a drying tube and a catalytic tube and finally into the $CO_2$ gas chamber, and then expelling the air in the $CO_2$ gas chamber through the exhaust port of the $CO_2$ gas chamber in a first time duration.

(2) $CO_2$ Concentration Measurement

The cylinder piston assembly is controlled to deliver pulmonary alveolus gas from the pulmonary alveolus gas bag into the $CO_2$ gas chamber through the gas channel for determining its $CO_2$ concentration.

(3) Gas Reversing

A. Pulmonary Alveolus Gas Reversing

The cylinder piston assembly is controlled to deliver the pulmonary alveolus gas from the pulmonary alveolus gas bag into the first reversing gas bag.

B. Gas Channel Cleaning

The air pump is controlled to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration.

C. Background Gas Reversing

The cylinder piston assembly is controlled to deliver background gas from the background gas bag into the second reversing gas bag through the gas channel.

D. Gas Channel Cleaning

The air pump is controlled to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration.

(4) CO Concentration Measurement

A. Gas Chamber Cleaning

The air pump is controlled to pump the external air into the gas channel through the drying tube and the catalytic tube and finally into the CO gas chamber, and then expelling the air in the CO gas chamber through the exhaust port of the CO gas chamber in a second time duration.

B. CO Concentration Measurement of the Background Gas

The background gas in the second reversing gas bag is delivered to the CO gas chamber with a small amount each time at an uniform velocity, or for multiple times of intermittence with a small amount each time at an uniform velocity for determining its CO concentration.

C. Gas Chamber Cleaning

The air pump is controlled to pump the external air into the gas channel through the drying tube and the catalytic tube and finally into the CO gas chamber, and then expelling the air in the CO gas chamber through the exhaust port of the CO gas chamber in a second time duration.

D. CO Concentration Measurement of the Pulmonary Alveolus Gas

The pulmonary alveolus gas in the first reversing gas bag is delivered by the cylinder piston to the CO gas chamber with a small amount each time at an uniform velocity, or for multiple times of intermittence with a small amount each time at an uniform velocity for determining its CO concentration.

E. Gas Channel Cleaning

The air pump is controlled to pump the external air into the gas channel through the drying tube and the catalytic tube and finally into the $CO_2$ gas chamber, and then expelling the air in the $CO_2$ gas chamber through the exhaust port of the $CO_2$ gas chamber in the first time duration.

(5) Gas Chamber Cleaning

The air pump is controlled to pump the external air into the gas channel through the drying tube and the catalytic tube and finally into the CO gas chamber, and then expelling the air in the CO gas chamber through the exhaust port of the CO gas chamber in the second time duration.

Before the start of the method for measuring the lifespan of a red blood cell according to the present application, the preparation of the pulmonary alveolus gas bag and the background gas bag, that is, the gas absorption process, are interpreted in detail as follows.

1. Pulmonary Alveolus Gas Collection (a) The subject handles a pulmonary alveolus gas collection device with a blower terminal close to his/her chest, takes a deep breath and then holds his/her breath for 10 to 20 seconds.

(b) The subject blows through the blower terminal after 10 to 20 seconds to breathe out all the gas inside his/her thoracic cavity.

(c) If the pulmonary alveolus gas bag is not filled with one breath (which means the pulmonary alveolus gas bag is caved for more than 1 cm when it is pressed by the hand), then the pulmonary alveolus gas bag is pressed for expelling all the gas inside and steps (a) and (b) are repeated until the pulmonary alveolus gas bag is full of the pulmonary alveolus gas.

(d) When the pulmonary alveolus gas bag is full, it is pulled off and covered, and then the pulmonary alveolus gas collection is completed.

2. Environment Background Gas Collection

The hand pump is pressed until the environment background gas is full of the air of where the subject locates (which means the environment background gas bag is caved for less than 1 cm when it is pressed by the hand). Then the hand pump is pulled off and covered, and the environment background gas collection is completed.

In the gas channel system having a serial number of i (i=1, 2, 3) in the method for measuring the lifespan of a red blood cell, the corresponding pulmonary alveolus gas bag, background gas bag, first reversing gas bag, and second reversing gas bag are respectively connected to the gas channel system via the solenoid valves Ei2, Ei3, Ei4, Ei5. The CO gas chamber and the $CO_2$ gas chamber shared by each gas channel system are respectively connected to one terminal of each gas channel system via the solenoid valves (E01, E02), while other terminal of the each gas channel system is connected with one terminal of the air pump whose other terminal is connected to an gas inlet of cleaning gas through the drying tube and catalytic tube.

Figure 2:
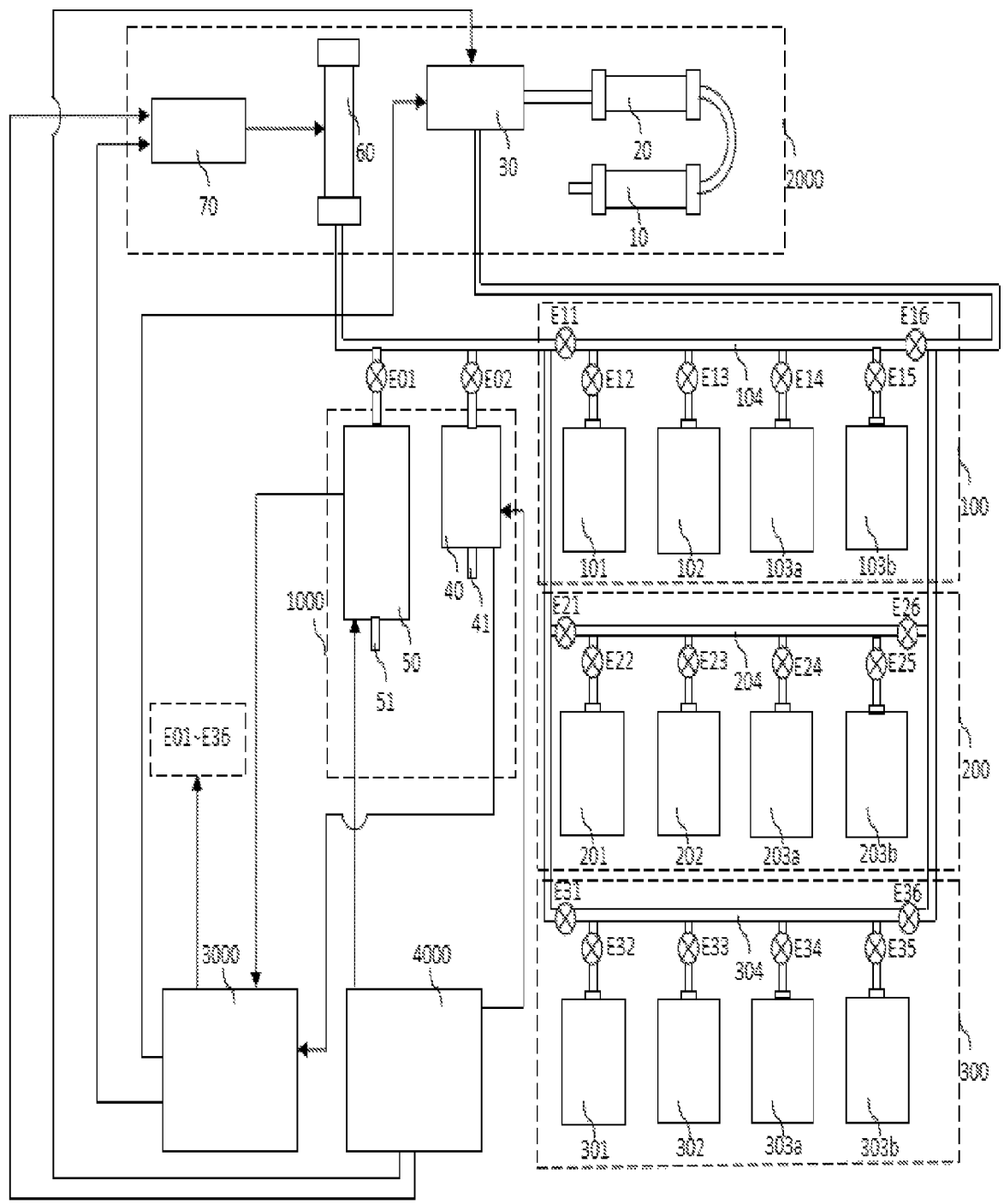
FIG. 2 is a schematic diagram of the device for measuring the lifespan of a red blood cell of the present application.

As another embodiment of the present application, a device for measuring the lifespan of a red blood cell is further provided and whose structure has been shown in FIG. 2. The device for measuring the lifespan of a red blood cell consists of a gas chamber unit 1000, a transmission unit 2000, a circuit unit 3000, a power source unit 4000, a cleaning gas preparation unit 5000, as well as a gas channel system and electrical connections connecting each unit. The gas chamber unit 1000 comprises one CO gas chamber assembly 50 and one $CO_2$ gas chamber assembly 40 both having an exhaust port and an inlet port with a solenoid valve. The transmission unit comprises a cylinder piston assembly 60 pushed by a lead screw, a stepper motor assembly 70 which drives the lead screw to rotate. The cleaning gas preparation unit comprises a gas pump assembly 30, a drying tube assembly 10 and a catalytic tube assembly 20, and the circuit unit 3000 comprises a signal amplification, data processing, and control circuit including a programmable chip. The power source unit 4000 provides an electric source for satisfying each unit. The gas channel refers to connection gas pipes (including the solenoid valve controlling the on-off state of the gas channel) in the assemblies in each unit or between the unit assemblies and the gas bags (the pulmonary alveolus gas bag, the background gas bag, the first reversing gas bag and the second reversing gas bag). The pulmonary alveolus gas bag is used for loading pulmonary alveolus gas sampled from the subjects. The background gas bag is used for loading environment gas sampled at the place where the subjects are located. The first and second reversing gas bags are used as an absorption bag for removing ingredients in the pulmonary alveolus gas and the environment gas which interfere CO measurement.

Each gas channel system comprises corresponding pulmonary alveolus gas bag, background gas bag, first reversing gas bag, and second reversing gas bag respectively connected to the gas channel system via the respective solenoid valve. For example, the first gas channel system 100 comprises "gas channel 1" 104, "pulmonary alveolus gas bag 1" 101, "background gas bag 1" 102, "first reversing gas bag 1" 103$a$ and "second reversing gas bag 2" 103$b$; the second gas channel system 200 comprises "gas channel 2" 204, "pulmonary alveolus gas bag 2" 201, "background gas bag 2" 202, "first reversing gas bag 2" 203$a$ and "second reversing gas bag 2" 203$b$; while the third gas channel system 300 comprises "gas channel 3" 304, "pulmonary alveolus gas bag 3" 301, "background gas bag 3" 302, "first reversing gas bag 3" 303$a$ and "second reversing gas bag 3" 303$b$. The present application can comprise multiple gas channel systems and so on and such examples would not be explained in detail for concise. For each gas channel system, its corresponding pulmonary alveolus gas bag, background gas bag, first reversing gas bag, and second reversing gas bag are respectively connected to the gas channel system via the solenoid valves (Ei2, Ei3, Ei4, Ei5). The CO gas chamber 50 and the $CO_2$ gas chamber 40 shared by each gas channel system are respectively connected to one terminal of each gas channel system via the solenoid valves (E01, E02), while other terminal of the each gas channel system is connected with one terminal of the air pump 30 whose other terminal is connected to an gas inlet of cleaning gas through the drying tube 20 and catalytic tube 10.

The device for measuring the lifespan of a red blood cell further comprises a control unit for each gas channel system to implement following steps S1-S6 sequentially.

S1) The gas channel and $CO_2$ gas chamber 40 are cleaned and the air pump 30 is controlled to pump external air into the gas channel through the drying tube 10 and the catalytic tube 20 and finally into the $CO_2$ gas chamber 40 through its inlet port, and then expel the air in the $CO_2$ gas chamber through the exhaust port 41 of the $CO_2$ gas chamber 40 in the first time duration.

S2) The cylinder piston assembly 60 is controlled to deliver pulmonary alveolus gas from the pulmonary alveolus gas bag into the $CO_2$ gas chamber 40 through the gas channel for determining its $CO_2$ concentration.

S3) The cylinder piston assembly 60 is controlled to deliver the pulmonary alveolus gas from the pulmonary alveolus gas bag into the first reversing gas bag.

S4) The gas channel and $CO_2$ gas chamber 40 are cleaned and the air pump 30 is controlled to pump the external air into the gas channel through the drying tube 10 and the catalytic tube 20 and finally into the $CO_2$ gas chamber 40 through its inlet port, and then expel the air in the $CO_2$ gas chamber through the exhaust port 41 of the $CO_2$ gas chamber 40 in the first time duration.

S5) The cylinder piston assembly 60 is controlled to deliver background gas from the background gas bag into the second reversing gas bag through the gas channel.

S6) The gas channel and $CO_2$ gas chamber 40 are cleaned and the air pump 30 is controlled to pump the external air into the gas channel through the drying tube 10 and the catalytic tube 20 and finally into the $CO_2$ gas chamber 40 through its inlet port, and then expel the air in the $CO_2$ gas chamber through the exhaust port 41 of the $CO_2$ gas chamber 40 in the first time duration.

After the implementation of the steps S1-S6, steps S7-S11 are implemented sequentially on each gas channel system.

S7) The gas channel and CO gas chamber 50 are cleaned and the air pump 30 is controlled to pump the external air into the gas channel through the drying tube 10 and the catalytic tube 20 and finally into the CO gas chamber 50 through its inlet port, and then expel the air in the CO gas chamber through the exhaust port 51 of the CO gas chamber 50 in a second time duration.

S8) The background gas in the second reversing gas bag is delivered by the cylinder piston assembly to the CO gas chamber 50 with a small amount each time at an uniform velocity, or for multiple times of intermittence with a small amount each time at an uniform velocity for determining its CO concentration.

S9) The gas channel and CO gas chamber 50 are cleaned and the air pump 30 is controlled to pump the external air into the gas channel through the drying tube 10 and the catalytic tube 20 and finally into the CO gas chamber 50 through its inlet port, and then expel the air in the CO gas chamber through the exhaust port 51 of the CO gas chamber 50 in the second time duration.

S10) The pulmonary alveolus gas in the first reversing gas bag to the CO gas chamber 50 through the cylinder piston assembly 60 with a small amount each time at an uniform velocity, or for multiple times of intermittence with a small amount each time at an uniform velocity for determining its CO concentration.

S11) The gas channel and $CO_2$ gas chamber 40 are cleaned and the air pump 30 is controlled to pump the external air into the gas channel through the drying tube 10 and the catalytic tube 20 and finally into the $CO_2$ gas chamber 40 through its inlet port, and then expelling the air in the $CO_2$ gas chamber through the exhaust port of the $CO_2$ gas chamber 40 in the first time duration.

After the implementation of the steps S7-S11, step S12 is implemented sequentially on the first gas channel system.

S12) The gas channel and CO gas chamber 50 are cleaned and the air pump 30 is controlled to pump the external air into the gas channel of the first gas channel system through the drying tube 10 and the catalytic tube 20 and finally into the CO gas chamber 50 through its inlet port, and then expel the air in the CO gas chamber through the exhaust port 51 of the CO gas chamber 50 in the second time duration.

Preferably, the first gas channel system 100 of the device for measuring the lifespan of a red blood cell is connected with the gas outlet of the air pump 30 through a solenoid valve E16. The first gas channel system 100 is communicated with the CO gas chamber 50 and the $CO_2$ gas chamber 40 shared by each gas channel system via the solenoid valve E11.

Embodiment 1

Single-channel pattern (taking the first channel for example)

(1) Gas Channel Cleaning

The solenoid valves E02, E11 and E16 are turned on and the remaining valves are turned off. Then the air pump is turned on for cleaning the gas channel for 60 seconds. (Cleaning process: Air→drying tube assembly 10→catalytic tube assembly 20→air pump 30-E16→"gas channel 1" 104→E11→E02→$CO_2$ gas chamber→exhaust port 41).

(2) $CO_2$ Concentration Measurement

The solenoid valves E12 and E11 are turned on and the remaining valves are turned off. Then the cylinder piston assembly extracts 200 ml pulmonary alveolus gas from the "pulmonary alveolus gas bag 1" 101. It should be noted that, although the present application takes 200 ml for example, one skilled in the art would know that the protection scope of the present application is not so limited. The solenoid valve E02 is turned on and the remaining valves are turned off. The cylinder piston assembly pumps 200 ml pulmonary alveolus gas into the $CO_2$ gas chamber for measurement. The $CO_2$ concentration measurement just requires a little sample gas and the remaining sample gas would be expelled through the exhaust port 41.

(3) Gas Reversing

A. Pulmonary Alveolus Gas Reversing

The solenoid valves E12 and E11 are turned on and the remaining valves are turned off. Then the cylinder piston assembly extracts 200 ml pulmonary alveolus gas from the "pulmonary alveolus gas bag 1" 101. It should be noted that, although the present application takes 200 ml for example, one skilled in the art would know that the protection scope of the present application is not so limited. The solenoid valves E14, E11 are turned on and the remaining valves are turned off. The cylinder piston assembly pumps 200 ml pulmonary alveolus gas into the "first reversing gas bag 1" 103a and the above steps are repeated for six times. In this embodiment, although the gas is pumped and sucked by the cylinder, it should be noted that gas pumping is just one option and there are other ways to pump or suck gas. The pumping times are not limited to six times and the present embodiment just takes it for example.

B. Gas Channel Cleaning

The solenoid valves E02, E11 and E16 are turned on and the remaining valves are turned off. Then the air pump is turned on for cleaning the gas channel for 60 seconds. (Cleaning process: Air→drying tube assembly 10→catalytic tube assembly 20→air pump 30-E16→"gas channel 1" 104→E11→E02→$CO_2$ gas chamber→exhaust port 41).

C. Background Gas Reversing

The solenoid valves E13 and E11 are turned on and the remaining valves are turned off. Then the cylinder piston assembly extracts 200 ml pulmonary alveolus gas from the "background gas bag 1" 102. The solenoid valves E15, E11 are turned on and the remaining valves are turned off. The cylinder piston assembly pumps 200 ml pulmonary alveolus gas into the "second reversing gas bag 1" 103a and the above steps are repeated for six times. In this embodiment, although the gas is pumped and sucked by the cylinder, it should be noted that gas pumping is just one option and there are other ways to pump or suck gas. The pumping times are not limited to six times and the present embodiment just takes it for example.

D. Gas Channel Cleaning

The solenoid valves E02, E11 and E16 are turned on and the remaining valves are turned off. Then the air pump is turned on for cleaning the gas channel for 60 seconds. (Cleaning process: Air→drying tube assembly 10→catalytic tube assembly 20→air pump 30-E16→"gas channel 1" 104→E11→E02→$CO_2$ gas chamber→exhaust port 41).

(4) CO Concentration Measurement

A. Gas Channel Cleaning

The solenoid valves E01, E11 and E16 are turned on and the remaining valves are turned off. Then the air pump is turned on for cleaning the gas chamber for 200 s. (Cleaning process: Air→drying tube assembly 10→catalytic tube assembly 20→air pump 30-E16→"gas channel 1" 104→E11→E01→CO gas chamber 50→exhaust port 51).

B. CO Concentration Measurement of the Background Gas

The solenoid valves E15 and E11 are turned on and the remaining valves are turned off. Then the cylinder piston assembly extracts 200 ml pulmonary alveolus gas from the "second reversing gas bag 2" 103b. The solenoid valve E01 is turned on and the remaining valves are turned off. Then the cylinder piston assembly pumps 200 ml pulmonary alveolus gas into the gas chamber and the above steps are repeated for five times. In this embodiment, although the gas is pumped for five times, it should be noted that it is for example rather than for limitation, and the pumping time can be 1-N times, and a period of time is required between two contiguous times of pumping.

C. CO Gas Chamber Cleaning

The solenoid valves E01, E11 and E16 are turned on and the remaining valves are turned off. Then the air pump is turned on for cleaning the gas chamber for 200 s. (Cleaning process: Air→drying tube assembly 10→catalytic tube assembly 20→air pump 30-E16→"gas channel 1" 104→E11→E01→CO gas chamber 50→exhaust port 51).

D. CO Concentration Measurement of the Pulmonary Alveolus Gas

The solenoid valves E14 and E11 are turned on and the remaining valves are turned off. Then the cylinder piston assembly extracts 200 ml pulmonary alveolus gas from the "first reversing gas bag 2" 103a. The solenoid valve E01 is turned on and the remaining valves are turned off. Then the cylinder piston assembly pumps 200 ml pulmonary alveolus gas into the gas chamber 50 and the above steps are repeated for five times. In this embodiment, although the gas is pumped for five times, it should be noted that it is for example rather than for limitation, and the pumping time can be 1-N times, and a period of time is required between two contiguous times of pumping.

E. Gas Channel Cleaning

The solenoid valves E02, E11 and E16 are turned on and the remaining valves are turned off. Then the air pump is turned on for cleaning the gas channel for 60 seconds (Cleaning process: Air→drying tube assembly 10→catalytic tube assembly 20→air pump 30-E16→"gas channel 1" 104→E11→E02→$CO_2$ gas chamber→exhaust port 41).

(5) Gas Chamber Cleaning

The solenoid valves E01, E11 and E16 are turned on and the remaining valves are turned off. Then the air pump is turned on for cleaning the gas chamber for 200 s. (Cleaning process: Air→drying tube assembly 10→catalytic tube assembly 20→air pump 30-E16→"gas channel 1" 104→E11→E01→CO gas chamber 50→exhaust port 51).

Embodiment 2

Multiple-Channel Pattern

1. $CO_2$ Concentration Measurement and Reversing in Channel I (i=1, 2, 3)

The following same steps are implemented for channel i=1, 2, 3.

(1) Gas Channel Cleaning

The solenoid valves E02, Ei1 and Ei6 are turned on and the remaining valves are turned off. Then the air pump is turned on for cleaning the gas channel for 60 seconds. (Cleaning process: Air→drying tube assembly 10→catalytic tube assembly 20→air pump 30-Ei6→gas channel i→Ei1→E02→$CO_2$ gas chamber 40→exhaust port 41).

(2) $CO_2$ Concentration Measurement

The solenoid valves Ei2 and Ei1 are turned on and the remaining valves are turned off. Then the cylinder piston assembly extracts 200 ml pulmonary alveolus gas from the "pulmonary alveolus gas bag i". The solenoid valve E02 is turned on and the remaining valves are turned off. The cylinder piston assembly pumps 200 ml pulmonary alveolus gas into $CO_2$ gas chamber 40 for measurement. The $CO_2$ concentration measurement just requires a little sample gas and the remaining sample gas would be expelled through the exhaust port 41.

(3) Gas Reversing

A. Pulmonary Alveolus Gas Reversing

The solenoid valves Ei2 and Ei1 are turned on and the remaining valves are turned off. Then the cylinder piston assembly extracts 200 ml pulmonary alveolus gas from the pulmonary alveolus gas bag i. It should be noted that, although the present application takes 200 ml for example, one skilled in the art would know that the protection scope of the present application is not so limited. The solenoid valves Ei4, Ei1 are turned on and the remaining valves are turned off. The cylinder piston assembly pumps 200 ml pulmonary alveolus gas into the first reversing gas bag i and the above steps are repeated for six times. In this embodiment, although the gas is pumped and sucked by the cylinder, it should be noted that gas pumping is just one option and there are other ways to pump or suck gas. The pumping times are not limited to six times and the present embodiment just takes it for example.

B. Gas channel cleaning

The solenoid valves E02, Ei1 and Ei6 are turned on and the remaining valves are turned off. Then the air pump is turned on for cleaning the gas channel for 60 seconds. (Cleaning process: Air→drying tube assembly 10→catalytic tube assembly 20→air pump 30-Ei6→gas channel i→Ei1→E02→$CO_2$ gas chamber→exhaust port 41).

C. Background Gas Reversing

The solenoid valves Ei3 and Ei1 are turned on and the remaining valves are turned off. Then the cylinder piston assembly extracts 200 ml pulmonary alveolus gas from the background gas bag i. The solenoid valves Ei5, Ei1 are turned on and the remaining valves are turned off. The cylinder piston assembly pumps 200 ml pulmonary alveolus gas into the second reversing gas bag i and the above steps are repeated for six times. In this embodiment, although the gas is pumped and sucked by the cylinder, it should be noted that gas pumping is just one option and there are other ways to pump or suck gas. The pumping times are not limited to six times and the present embodiment just takes it for example.

D. Gas Channel Cleaning

The solenoid valves E02, Ei1 and Ei6 are turned on and the remaining valves are turned off. Then the air pump is turned on for cleaning the gas channel for 60 seconds. (Cleaning process: Air→drying tube assembly 10→catalytic tube assembly 20→air pump 30-Ei6→gas channel i→Ei1→E02→$CO_2$ gas chamber→exhaust port 41).

2. CO Concentration Measurement for Channel i=1, 2, 3.

The following same steps are implemented for channel i=1, 2, 3.

(1). Gas Channel Cleaning

The solenoid valves E01, Ei1 and Ei6 are turned on and the remaining valves are turned off. Then the air pump is turned on for cleaning the gas chamber for 200 s. (Cleaning process: Air→drying tube assembly 10→catalytic tube assembly 20→air pump 30-Ei6→gas channel i→Ei1→E01→CO gas chamber 50→exhaust port 51).

(2). CO Concentration Measurement of the Background Gas

The solenoid valves Ei5 and Ei1 are turned on and the remaining valves are turned off. Then the cylinder piston assembly extracts 200 ml pulmonary alveolus gas from the second reversing gas bag i. The solenoid valve E01 is turned on and the remaining valves are turned off. Then the cylinder piston assembly pumps 200 ml pulmonary alveolus gas into the gas chamber and the above steps are repeated for five times. In this embodiment, although the gas is pumped for five times, it should be noted that it is for example rather than for limitation, and the pumping time can be 1-N times, and a period of time is required between two contiguous times of pumping.

(3). Gas Chamber Cleaning

The solenoid valves E01, Ei1 and Ei6 are turned on and the remaining valves are turned off. Then the air pump is turned on for cleaning the gas chamber for 200 s. (Cleaning process: Air→drying tube assembly 10→catalytic tube assembly 20→air pump 30-Ei6→gas channel i→Ei1→E01→CO gas chamber 50→exhaust port 51).

(4). CO Concentration Measurement of the Pulmonary Alveolus Gas

The solenoid valves Ei4 and Ei1 are turned on and the remaining valves are turned off. Then the cylinder piston assembly extracts 200 ml pulmonary alveolus gas from the first reversing gas bag i. The solenoid valve E01 is turned on and the remaining valves are turned off. Then the cylinder piston assembly pumps 200 ml pulmonary alveolus gas into the gas chamber and the above steps are repeated for five times. In this embodiment, although the gas is pumped for five times, it should be noted that it is for example rather than for limitation, and the pumping time can be 1-N times, and a period of time is required between two contiguous times of pumping.

(5) Gas Channel Cleaning

The solenoid valves E01, Ei1 and Ei6 are turned on and the remaining valves are turned off. Then the air pump is turned on for cleaning the gas channel for 60 s. (Cleaning process: Air→drying tube assembly 10→catalytic tube assembly 20→air pump 30-Ei6→gas channel i→Ei1→E02→$CO_2$ gas chamber 40→exhaust port 41).

3. Gas Chamber Cleaning

The solenoid valves E01, E11 and E16 are turned on and the remaining valves are turned off. Then the air pump is turned on for cleaning the gas chamber for 200 s. (Cleaning process: Air→drying tube assembly 10→catalytic tube assembly 20→air pump 30-E16→gas channel 1→E11→E01→CO gas chamber 50→exhaust port 51).

Although the embodiments of the present application are described in combination with the accompanying drawings, however the present application is not limited to the specific implementation methods mentioned above. Moreover the specific implementation methods are merely schematic rather than restrictive, and one skilled in the art would make many modifications under the inspiration of the present application without departing from the purpose and the protection scope of the present application. All these modifications fall into the protection scope of the present application.

What is claimed is:

1. A method for measuring a lifespan of a red blood cell employing at least one gas channel system each comprising a gas channel; a pulmonary alveolus gas bag, a background gas bag, a first reversing gas bag and a second reversing gas bag respectively connected to the gas channel via a respective solenoid valve; wherein each gas channel is connected to a same CO gas chamber, $CO_2$ gas chamber, cylinder piston assembly and air pump, wherein both of the CO gas chamber and the $CO_2$ gas chamber have an exhaust port and an inlet port with a solenoid valve, wherein the method for measuring the lifespan of a red blood cell comprises following steps implemented sequentially:

S1) controlling the air pump to pump external air into the gas channel through a drying tube and a catalytic tube and finally into the $CO_2$ gas chamber through its inlet port, and then expelling the air in the $CO_2$ gas chamber through the exhaust port of the $CO_2$ gas chamber in a first time duration;

S2) controlling the cylinder piston assembly to deliver pulmonary alveolus gas from the pulmonary alveolus gas bag into the $CO_2$ gas chamber through the gas channel for determining its $CO_2$ concentration;

S3) controlling the cylinder piston assembly to deliver the pulmonary alveolus gas from the pulmonary alveolus gas bag into the first reversing gas bag through the gas channel;

S4) controlling the air pump to pump the external air into the gas channel through the drying tube and the catalytic tube and finally into the $CO_2$ gas chamber, and then discharge the same from the exhaust port of the $CO_2$ gas chamber in the first time duration;

S5) controlling the cylinder piston assembly to deliver background gas from the background gas bag into the second reversing gas bag through the gas channel;

S6) controlling the air pump to pump the external air into the gas channel through the drying tube and the catalytic tube and finally into the $CO_2$ gas chamber through its inlet port, and then expelling the air in the $CO_2$ gas chamber through the exhaust port of the $CO_2$ gas chamber in the first time duration;

wherein the method for measuring the lifespan of a red blood cell further comprising following steps S7-S11 implemented sequentially on each gas channel system after the implementation of the steps S1-S6:

S7) controlling the air pump to pump the external air into the gas channel through the drying tube and the catalytic tube and finally into the CO gas chamber through its inlet port, and then expelling the air in the CO gas chamber through the exhaust port of the CO gas chamber in a second time duration;

S8) delivering the background gas in the second reversing gas bag to the CO gas chamber with a small amount each time at an uniform velocity, or for multiple times of intermittence with a small amount each time at an uniform velocity for determining its CO concentration; wherein each time of gas delivery has a third time duration, and each intermittence of the multiple injections has a fourth time duration;

S9) controlling the air pump to pump the external air into the gas channel through the drying tube and the catalytic tube and finally into the CO gas chamber through its inlet port, and then expelling the air in the CO gas chamber through the exhaust port of the same CO gas chamber in a second time duration;

S10) controlling the cylinder piston assembly to deliver the pulmonary alveolus gas in the first reversing gas bag to the CO gas chamber with a small amount each time at an uniform velocity, or for multiple times of intermittence with a small amount each time at an uniform velocity for determining its CO concentration; wherein each time of gas delivery has the third time duration, and each intermittence of the multiple injections has the fourth time duration;

S11) controlling the air pump to pump the external air into the gas channel through the drying tube and the catalytic tube and finally into the $CO_2$ gas chamber through its inlet port, and then expelling the air in the $CO_2$ gas chamber through the exhaust port of the $CO_2$ gas chamber in the first time duration;

wherein the method for measuring the lifespan of a red blood cell further comprising following step S12 implemented on a first gas channel system after the implementation of the steps S7-S11:

S12) controlling the air pump to pump the external air into the gas channel of the first gas channel system through the drying tube and the catalytic tube and finally into the CO gas chamber through its inlet port, and then expelling the air in the CO gas chamber through the exhaust port of the same CO gas chamber in a second time duration;

after implementing steps S1-S12, correcting an influence of air mixed during a pulmonary alveolus gas sampling implemented by Step S8 on an endogenous CO concentration obtained in step S10 by the $CO_2$ concentration determined in step S2; and then calculating the lifespan of the red blood cell based on corrected endogenous CO concentration.

2. The method for measuring the lifespan of a red blood cell according to claim 1, wherein the first time duration is 6-600s which is in order to clean the $CO_2$ gas chamber until the $CO_2$ gas chamber is full of cleaning gas, the second time duration is 20-2000s which is in order to clean the CO gas chamber until the CO gas chamber is full of cleaning gas, the third time duration is 1-90s which is in order to deliver the detected gas sample into the CO gas chamber at an uniform velocity, and the fourth time duration is 1-100s which is in order to make the detected gas sample mixed with the original gas in the CO gas chamber evenly.

3. The method for measuring the lifespan of a red blood cell according to claim 1, wherein for the i-th (i=1,2,3, . . . ,N) gas channel system, its corresponding pulmonary alveolus gas bag, background gas bag, first reversing gas bag and second reversing gas bag are respectively connected to the gas channel system via the solenoid valves.

4. The method for measuring the lifespan of a red blood cell according to claim 3, wherein the CO gas chamber and the $CO_2$ gas chamber shared by each gas channel system are respectively connected to one terminal of each gas channel system via the solenoid valves, while other terminal of the each gas channel system is connected with one terminal of the air pump whose other terminal is connected to an gas inlet of cleaning gas through the cleaning gas preparation unit which has assemblies of the drying tube and catalytic tube connected in series with a random order.

5. The method for measuring the lifespan of a red blood cell according to claim 1, wherein in step S3, delivering the pulmonary alveolus gas into the first reversing gas bag comprises multiple times of deliveries or one time of delivery; in step S5 delivering the background gas into the second reversing gas bag comprises multiple times of deliveries or one time of delivery.

6. The method for measuring the lifespan of a red blood cell according to claim 1, wherein the cylinder piston assembly further comprises a lead screw, a cylinder communicating with the CO gas chamber and the $CO_2$ gas chamber shared by each gas channel system, a piston-piston rod displaced inside the cylinder, a sliding block driving the piston rod to move along the screw rod in a reciprocating motion, and an electrical motor whose output shaft drives the sliding block to move the screw rod along a displacement of the lead screw.

7. The method for measuring the lifespan of a red blood cell according to claim 1, wherein for each gas channel system, its corresponding pulmonary alveolus gas bag, background gas bag, first reversing gas bag, second reversing gas bag are respectively connected to a specific gas channel via the solenoid valves; the CO gas chamber and the $CO_2$ gas chamber shared by each gas channel system are respectively connected to a section of a common gas channel which is shared by all the gas channel systems at one terminal of the gas channel system via the solenoid valves; the cylinder of the cylinder piston assembly shared by each gas channel system is connected to the section of the common gas channel which is shared by all the gas channel systems at the same terminal of each gas channel system, and the other terminal of each gas channel system is connected to one terminal of the gas pump via a section of the common gas channel, and the other terminal of the gas pump is connected to the gas inlet of the cleaning gas preparation unit through the cleaning gas preparation unit itself.

8. The method for measuring the lifespan of a red blood cell according to claim 1, wherein one terminal of a specific gas channel of each gas channel system is connected with the cleaning gas preparation unit via a respective solenoid valve, and the other terminal of which is connected with the cylinder via a respective solenoid valve through one section of a common gas channel.

9. A device for measuring the lifespan of a red blood cell comprising a gas chamber unit, a transmission unit, a circuit unit, a power source unit, a cleaning gas preparation unit, as well as a gas channel system and electrical connections connecting each unit; wherein the gas chamber unit comprises a CO gas chamber assembly and a $CO_2$ gas chamber assembly which are both provided with an exhaust port and an inlet port with a solenoid valve; the transmission unit comprises a cylinder piston assembly pushed by a lead screw, a stepper motor assembly which drives the lead screw to rotate; the cleaning gas preparation unit comprises a gas pump assembly, a drying tube assembly and a catalytic tube assembly; and the circuit unit comprises a signal amplification, data processing, and control circuit including a programmable chip; the power source unit provides an electric source for satisfying each unit; the gas channel system consists of gas channels which comprise connection gas pipes in assemblies in each unit or between the unit assemblies and gas bags, and solenoid valves controlling an on-off state of the gas channel; wherein the gas bag comprises a pulmonary alveolus gas bag used for loading pulmonary alveolus gas sampled from subjects, a background gas bag used for loading environment gas sampled at a place where the subjects are located, a first and second reversing gas bags used as an absorption bag for removing ingredients in the pulmonary alveolus gas and the environment gas which interfere CO measurement; wherein the pulmonary alveolus gas bag, the background gas bag, the first reversing gas bag and the second reversing gas bag which are connected with the gas chamber unit, the transmission unit and the cleaning gas preparation unit via the gas channels together form one measurement channel.

10. The device for measuring the lifespan of a red blood cell according to claim 9, wherein comprises one gas channel system or multiple gas channel systems, wherein the gas channels inside the multiple gas channel systems are divided into a common gas channel which can be share by two or more gas channel system and a specific gas channel which can only be used by one gas channel system, wherein the specific gas channel is a gas channel which is required for completing a lifespan measurement of the red blood cell once and connected to each gas bag via a respective solenoid valve.

11. The device for measuring the lifespan of a red blood cell according to claim 9, wherein for each gas channel system, corresponding pulmonary alveolus gas bag, background gas bag, first and second reversing gas bags are respectively connected to the gas channel via a respective solenoid valve.

12. The device for measuring the lifespan of a red blood cell according to claim 9, wherein the CO gas chamber and the $CO_2$ gas chamber shared by each gas channel system are respectively connected to one terminal of each gas channel system via the solenoid valves, while other terminal of the each gas channel system is connected with the cleaning gas preparation unit and through which further connected to an gas inlet of cleaning gas, wherein the cleaning gas preparation unit has assemblies of the drying tube and catalytic tube connected in series with a random order.

13. The device for measuring the lifespan of a red blood cell according to claim 12, wherein the other terminal of the each gas channel system is connected with one terminal of the air pump of the cleaning gas preparation unit whose other terminal is connected to a drying tube assembly which is further connected to the gas inlet of the cleaning gas preparation unit through a catalytic tube.

14. The device for measuring the lifespan of a red blood cell according to claim 9, wherein the cylinder piston assembly further comprises a lead screw, a cylinder communicating with the CO gas chamber and the $CO_2$ gas chamber shared by each gas channel system, a piston-piston rod displaced inside the cylinder, a sliding block driving the piston rod to move along the screw rod in a reciprocating motion, and an electrical motor whose output shaft drives the sliding block to move the screw rod along a displacement of the lead screw.

15. The device for measuring the lifespan of a red blood cell according to claim 10, wherein one terminal of the specific gas channel of each gas channel system is connected with the cleaning gas preparation unit via a respective solenoid valve through one section of a common gas channel, and the other terminal of which is connected with the cylinder via a respective solenoid valve through one section of a common gas channel.

16. The device for measuring the lifespan of a red blood cell according to claim 10, wherein the CO gas chamber and the $CO_2$ gas chamber shared by each gas channel system are respectively connected to the specific gas channel of each gas channel system and a section of the common gas channel of the cylinder which is shared by all the gas channel systems.

17. A method for measuring the lifespan of a red blood cell comprising following steps: preparing cleaning gas to clean gas chamber until the gas chamber is full of cleaning gas; delivering gas sample to be determined with a small amount each time at an uniform velocity, or for multiple times of intermittence with a small amount each time at an uniform velocity to the gas chamber; removing interference components by an interference component absorption bag; obtaining endogenous CO concentration of pulmonary alveolus gas from pulmonary alveolus gas sample and background gas sample by a pair of measurements which are implemented closely in time via a pair of level difference-concentration difference fitting method; measuring CO concentration and $CO_2$ concentration by a same instrument simultaneously via a double-gas chamber method using a CO gas chamber and a $CO_2$ gas chamber and correcting an influence of air mixed during a pulmonary alveolus gas sampling process according to the measured $CO_2$ concentration to obtain an accurate value of the endogenous CO concentration of the pulmonary alveolus gas for finally calculating the lifespan of the red blood cell; calculating the lifespan of the red blood cell based on the accurate value of the endogenous CO concentration.

18. The method for measuring the lifespan of a red blood cell according to claim 17, wherein comprising following steps:

step 1, preparing the cleaning gas of stable performance via the drying tube and catalytic tube and cleaning the gas chamber until the gas chamber is full of cleaning gas;

step 2, pumping a small portion of pulmonary alveolus gas sample via the transmission unit into the $CO_2$ gas chamber of the double-gas chamber for determining $CO_2$ concentration in the pulmonary alveolus gas sample;

step 3, delivering the gas sample into the reversing gas bag and employing the absorption bag for removing ingredients;

step 4, delivering the gas sample into the CO gas chamber with a small amount each time at a uniform velocity or for multiple times of intermittence with a small amount each time at an uniform velocity;

step 5, obtaining endogenous CO concentration of the pulmonary alveolus gas from a level difference-concentration difference between the measured pulmonary alveolus gas and the background gas through a difference-concentration difference fitting method;

step 6, correcting the influence of air mixed during the pulmonary alveolus gas sampling on the endogenous CO concentration of the pulmonary alveolus gas according to the measured $CO_2$ concentration and calculating the lifespan of the red blood cell based on the accurate value of the endogenous CO concentration of the pulmonary alveolus gas.

19. The method for measuring the lifespan of a red blood cell according to claim 18, wherein the cleaning gas can be prepared by a cleaning gas preparation unit installed inside the device for measuring the lifespan of a red blood cell, or external independent preparation system, or is obtained by outsourcing; the small amount means a volume which is 1/100-5 times of that of the gas chamber and less than 2 liters, the uniform velocity means a pumping velocity of the pulmonary alveolus gas which is uniform and is also exactly the same as that of the background gas; when one injection volume is much less than the volume of the CO gas chamber, the multiple times means 2-100 times while intermittence means an intermittence of 1-100 seconds between contiguous two injections.

20. The method for measuring the lifespan of a red blood cell according to claim 18, wherein the interference component absorption bag is an absorption bag containing an absorbing material, or a filter absorber containing an absorbent, or is disposable or can be replaced after a period or a certain times of use; wherein the pair of measurements for the pulmonary alveolus gas and the background gas can comprise measuring the pulmonary alveolus gas at first and then the background gas, or vice-versa, as if the same order is employed during the standard gas calibration and the lifespan measurement of the red blood cell; wherein the difference-concentration difference fitting method can be a least square method or other curve fitting methods.

\* \* \* \* \*